United States Patent [19]

Stark

[11] Patent Number: 5,456,267
[45] Date of Patent: Oct. 10, 1995

[54] BONE MARROW HARVESTING SYSTEMS AND METHODS AND BONE BIOPSY SYSTEMS AND METHODS

[76] Inventor: John G. Stark, 19390 Walden Tr., Deephaven, Minn. 55391

[21] Appl. No.: 214,620

[22] Filed: Mar. 18, 1994

[51] Int. Cl.⁶ .............................. A61B 17/58; A61F 5/04
[52] U.S. Cl. .............................. 128/898; 606/65
[58] Field of Search ..................... 128/749, 752, 128/758, 897, 898, 754; 604/35, 49, 175, 188; 606/53, 98, 180, 65; 408/14, 112; 175/40, 292

[56] References Cited

U.S. PATENT DOCUMENTS

| | | |
|---|---|---|
| 2,242,003 | 5/1941 | Lorenzo . |
| 2,414,882 | 1/1947 | Longfellow . |
| 2,570,465 | 10/1951 | Lundholm . |
| 2,631,584 | 3/1953 | Purificato . |
| 3,915,162 | 10/1975 | Miller . |
| 3,990,438 | 11/1976 | Pritchard . |
| 4,132,496 | 1/1979 | Casto .................. 408/112 |
| 4,175,555 | 11/1979 | Herbert . |
| 4,414,966 | 11/1983 | Stednitz . |
| 4,537,185 | 8/1985 | Stednitz . |
| 4,913,134 | 4/1990 | Luque . |
| 4,913,137 | 4/1990 | Azer et al. . |
| 4,922,897 | 5/1990 | Sapega et al. . |
| 4,927,421 | 5/1990 | Goble et al. . |
| 4,940,467 | 7/1990 | Tronzo . |
| 4,963,144 | 10/1990 | Huene . |
| 4,978,350 | 12/1990 | Wagenknecht . |
| 5,019,079 | 5/1991 | Ross . |
| 5,019,080 | 5/1991 | Hemer . |
| 5,047,030 | 9/1991 | Draenert . |
| 5,098,434 | 3/1992 | Serbousek . |
| 5,129,901 | 7/1992 | Decoste .................. 606/65 |

OTHER PUBLICATIONS

Photographs of a Jamshidi device, Exhibit A.
Photographs of a Monoject® device, Exhibit B.
Copy of a Monoject® device packaging, one page dated 1991, Exhibit C.

*Primary Examiner*—Lee S. Cohen
*Assistant Examiner*—Stephen Huang
*Attorney, Agent, or Firm*—Merchant, Gould, Smith, Edell, Welter & Schmidt

[57] ABSTRACT

The invention relates to systems and methods for harvesting bone marrow and biopsy sections of bone. A hollow screw is attached to the bone and then a negative pressure is applied to the screw to withdraw the bone marrow through the hollow portion of the screw. One system and method includes inserting a pin into the bone and then positioning the screw on the pin. A guide cannula may be used to insert the pin. The screw is inserted into the bone and then the pin withdrawn, leaving the screw in the bone to withdraw the bone marrow. Another system and method includes using a screw with a head end and an opposing threaded end, with the threaded end being provided with cutting flutes or partial or full missing threads, or both, and then withdrawing the bone marrow from voids created by the flutes or the missing threads. Another system and method includes rotating a self-drilling and self-tapping screw into the bone without the use of a pin, and then withdrawing the bone marrow through side ports in the screw from a void created by partial or full missing threads on the screw. Another system and method is provided for bone biopsy procedures wherein a screw is positioned in the bone and a cannula is subsequently provided to create a bone core between the screw and the cannula which can be analyzed.

24 Claims, 12 Drawing Sheets

FIG. IIA
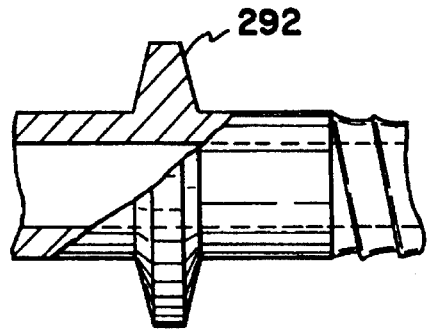
FIG. IIB
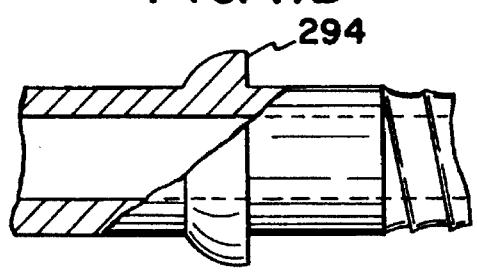
FIG. IIC
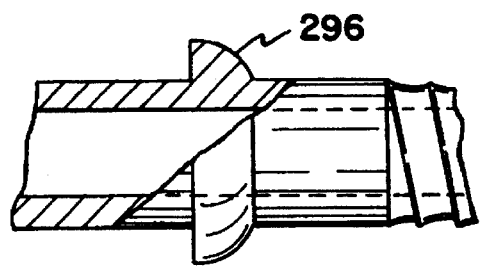
FIG. 14
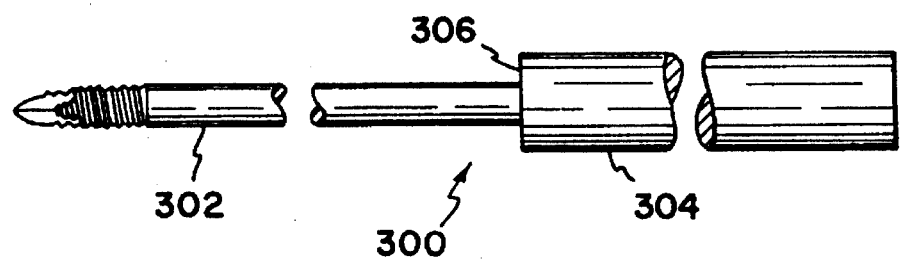

5,456,267

BONE MARROW HARVESTING SYSTEMS AND METHODS AND BONE BIOPSY SYSTEMS AND METHODS

FIELD OF THE INVENTION

The present invention relates to systems and methods for harvesting, collecting or removing bone marrow from bones for such purposes as bone marrow transplants between donor and recipient patients, bone marrow biopsies, bone graftings, and research harvesting. The present invention also relates to systems and methods for removing bone samples such as in bone biopsies.

BACKGROUND OF THE INVENTION

Surgical techniques are known for harvesting bone marrow from the interior of bones from humans or animals. One known technique for harvesting bone marrow from live human donor patients includes insertion of a first end of a tube through the exterior surface of a bone into the interior of the bone. Following insertion of the tube, a negative pressure is applied to the second, opposite end of the tube to withdraw bone marrow from the bone.

The results of this technique have often been inadequate. One reason is that bone marrow is difficult to remove from donor patients by applying the negative pressure to a tube inserted in this manner.

Bone marrow harvesting surgeries are often uncomfortable, and even quite painful, for the patient. One concern in this area is to perform the harvesting operation as efficiently as possible without causing undue discomfort and pain to the donor patient. Also, there is a concern in obtaining the bone marrow without exposing the patient to unnecessary risks of harm or permanent damage by removing the bone marrow. A further concern is that the harvesting operation produce harvested bone marrow having a sufficiently good quality for use in bone marrow transplants to recipient patients.

A need exists in the prior art for systems and methods which permit bone marrow harvesting and which address at least some or all of the various concerns noted above and other concerns.

It is also desireable in some situations to gather bone samples, such as bone cores, as part of bone biopsy procedures. A need exists for systems and methods which permit consistent and reliable bone biopsies to gather bone samples of sufficiently good quality for analysis. There is a further need for systems and methods for removing the bone samples from the patient which does not expose the patient to excessive pain, discomfort, or a high risk of complications.

SUMMARY OF THE INVENTION

One aspect of the present invention relates to systems and methods for harvesting bone marrow from a bone. One method comprises inserting a pin into the bone to a desired depth and then turning a screw around the pin to insert the screw into the bone. Once the screw is operatively positioned in the bone, the pin is removed and bone marrow is withdrawn from the bone. The pin may be extended further into the bone than the screw, such that a void is created adjacent the tip of the screw when the pin is withdrawn. The screw may also include cutting flutes or missing threads for creating further voids in the bone to facilitate withdrawal of bone marrow. The screw may be partially withdrawn to create a further void adjacent the screw tip.

A related method for harvesting bone marrow may further include providing a cannula with structure to engage the bone to prevent slipping of the cannula relative to the bone when the cannula tip is engaged with the bone. The cannula is utilized during initial set up to help guide the pin into the bone.

The pin may be provided with a stop structure to limit the amount of insertion of the pin into the bone, whether the pin is inserted with a guide cannula or without. The stop structure may be adjusted on the pin to stop pin insertion at one of a plurality of different depths.

Another method of bone marrow harvesting is provided where a self-drilling and self-tapping screw is driven into the bone with rotational motion without the use of a guide pin. The screw is provided with a partial axial bore that terminates in one or more side ports in lateral side portions of the screw from which bone marrow can enter the axial bore of the screw from the bone.

Various embodiments of cannulas, pins, and screws are disclosed. Variations with respect to the cannula include bone-engaging structures having at least one tooth or a plurality of teeth. Variations of the pin include stop structure, some of which is adjustable. Variations with respect to the screw include providing an axial bore that extends all the way through the screw from one end to the other, or providing at least one side port, with or without the axial bore extending all the way through the tip. Other variations of the screw include extension structure for extending the screw away from the bone such that interference with skin and other tissue surrounding the bone is avoided when the screw is operatively positioned in the bone. Further embodiments of the screw are disclosed which permit twisting attachment of a wrench to the screw to facilitate insertion, and later removal, of the screw. Cutting flutes may also be provided to facilitate withdrawal of greater amounts of bone marrow. Other variations of the screw include removing threads, and possibly a portion of the shaft, adjacent the side ports provided in the screw such that the threads located adjacent the tip will have created a void region adjacent the side port from which the side port can withdraw the bone marrow. In a further embodiment, a second thread may be provided between the threads of the first thread. The second thread may periodically terminate or become smaller in some dimension, thereby creating a void for withdrawing the bone marrow. Various methods are disclosed for using the various different embodiments of the cannula, pin, and screw designs.

It is believed the various embodiments and features disclosed herein address a significant problem of conventional bone marrow harvesting techniques. The problem of the conventional techniques relates to an insufficient amount of bone marrow locations being exposed to the vacuum source. A tube merely inserted into the bone exposes very little surface area of bone interior to the vacuum source. Generally, in the conventional technique using a tube, the amount of surface area of exposed bone interior is roughly equal to the inner bore of the tube. In the present invention, the various voids or wells increase surface area of bone interior exposed to the vacuum source. The voids, either singularly or in combination, may be formed by structures such as the pin, the cutting flutes, the missing or removed threads, or the partially withdrawn screw. It is believed the voids which are created permit the bone marrow to be extracted more efficiently and at a greater volume than is otherwise possible with conventional techniques due to the larger surface area of the interior bony elements exposed to the vacuum source.

In another aspect of the invention, the screw may be useful for measuring intraosseous pressure or administering systemic medication once the screw is operatively positioned in the bone.

In still further aspects of the invention, systems and methods are provided for gathering a bone sample, such for a bone biopsy procedure. A screw is provided which is threadably received by the bone by first threads on a first end of the screw. A separate cannula is provided which is positioned around the screw such that the screw is received in an inner passage of the cannula. Threads on the cannula located on the inner passage engage second threads provided on an exterior surface of the screw on a second end of the screw. The cannula is rotated relative to the screw and into the bone until further rotation is stopped by stop structure. Upon further attempted rotation of the cannula, the rotational force is transmitted to the screw wherein a bone core positioned between the screw and the cannula is snapped off adjacent the tip region of the screw and the end of the cannula such that the bone core can be removed from the bone when the screw and the cannula are removed. Once the screw and the cannula are removed, the screw can be separated from the cannula to access the bone core for analysis.

BRIEF DESCRIPTION OF THE DRAWINGS

Throughout the following views, reference numerals will be used on the drawings, and the same reference numerals will be used throughout the several views and in the description to indicate same or like parts of the invention:

FIG. 11A is a view of a portion of a second alternative screw in cross-section;

FIG. 11B is a view of a portion of a third alternative screw in partial cross-section;

FIG. 11C is a view of a portion of a fourth alternative screw in partial cross-section;

FIG. 14 is a view of a second alternative pin, with portions removed;

DETAILED DESCRIPTION OF THE PRIOR ART AND THE PREFERRED EMBODIMENTS

Figure 1:
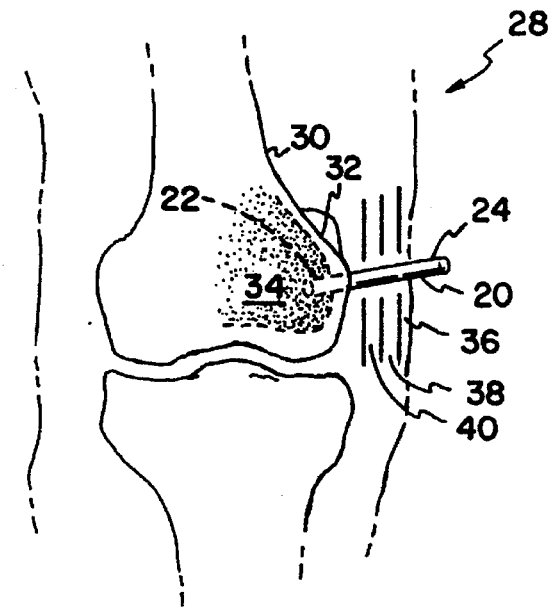
FIG. 1 is a view of a prior art system for harvesting bone marrow.

FIG. 1 relates to a prior art bone marrow harvesting system and method. A first end 22 of tube 20 is inserted into the bone 30 of leg 28 through the exterior surface 32 of the bone to the interior region 34 of the bone. A vacuum source, or negative pressure source (not shown) is applied to a second end 24 of the tube 20 to withdraw bone marrow through the tube. Bone 30 is part of a human donor's leg 28. Skin 36, a layer of fat 38, and a tendon 40 typically cover the exterior surface of bone 30 in the knee region of leg 28 show in FIG. 1.

FIGS. 2–23 illustrate various features of systems and methods according to the present invention for use in harvesting bone marrow.

Figure 2:
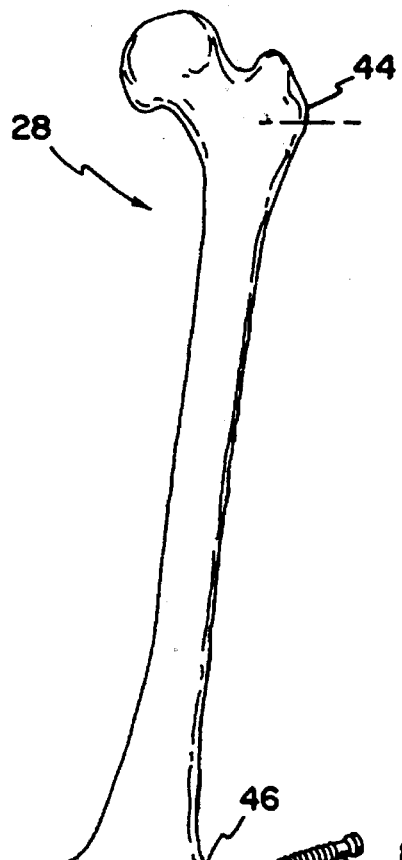
FIG. 2 is a view of a human leg showing several locations where bone marrow can be harvested as part of the present invention.

FIG. 2 illustrates a portion of a typical human donor's leg 28. FIG. 2 also illustrates three possible locations for bone marrow harvesting according to the present invention. A first possible bone marrow harvesting site is at the greater trochanter region, or proximal femoral metaphysis region 44. A second site is at the lateral femoral condyle region, or lateral femoral metaphysis region 46. A third site is at the proximal tibia region, or proximal tibial metaphysis region 48. It is believed that the lateral side 50 of leg 28 at sites 44, 46, 48 is preferred to avoid neurovascular structures as much as possible. Problems can result if nerves are damaged during a bone marrow harvesting operation. It is to be appreciated that other locations, both in the leg and at other locations in the human body, are possible sites for bone marrow harvesting. For example, the iliac crest and sternum are other sites for harvesting bone marrow.

Figure 3:
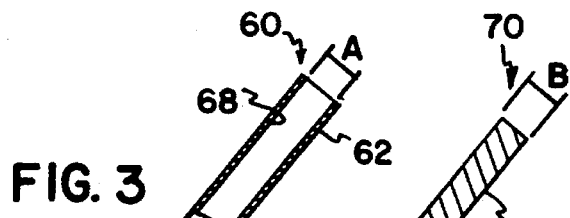
FIG. 3 is a view of an embodiment of a cannula in partial cross-section, with a portion removed.

FIG. 3 shows a cannula, or sleeve 60, including a first end 62 and a second end 64. Second end 64 is provided with a plurality of teeth 66. Cannula 60 has a minimum inside diameter 68 represented by dimension A.

Figure 13A:
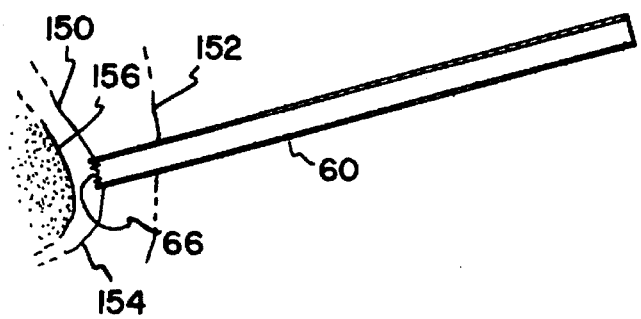
FIGS. 13 A–F illustrate various steps in one method according to the present invention for harvesting bone marrow.
Figure 13B:
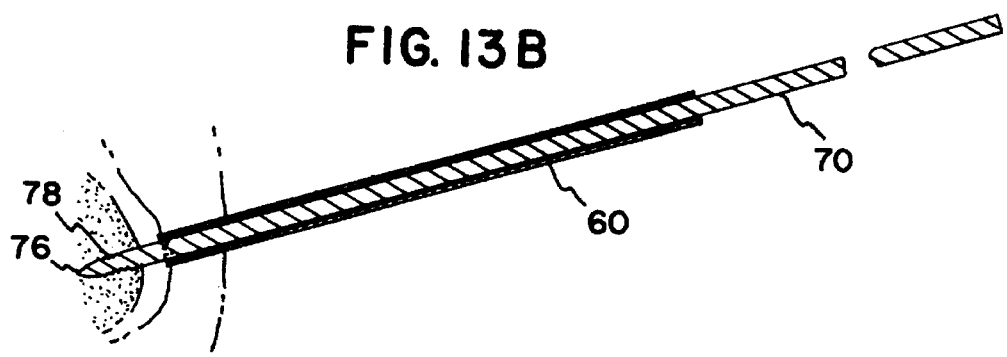

Cannula 60 is provided to guide a pin 70 through inside diameter 68 toward the appropriate location in the bone (see FIG. 13B, for example). A controlled insertion of the pin may be desirable in a bone marrow harvesting operation. Teeth 66 are provided to engage the exterior surface of the bone (see FIGS. 13A and B, for example). Teeth 66 on cannula 60 help to prevent second end 64 of cannula 60 from sliding or moving relative to the exterior surface of the bone during insertion of the pin into the bone. Cannula 60 may be constructed from any of a variety of medically approved materials. One preferred material is metal, such as stainless steel.

Figure 4:
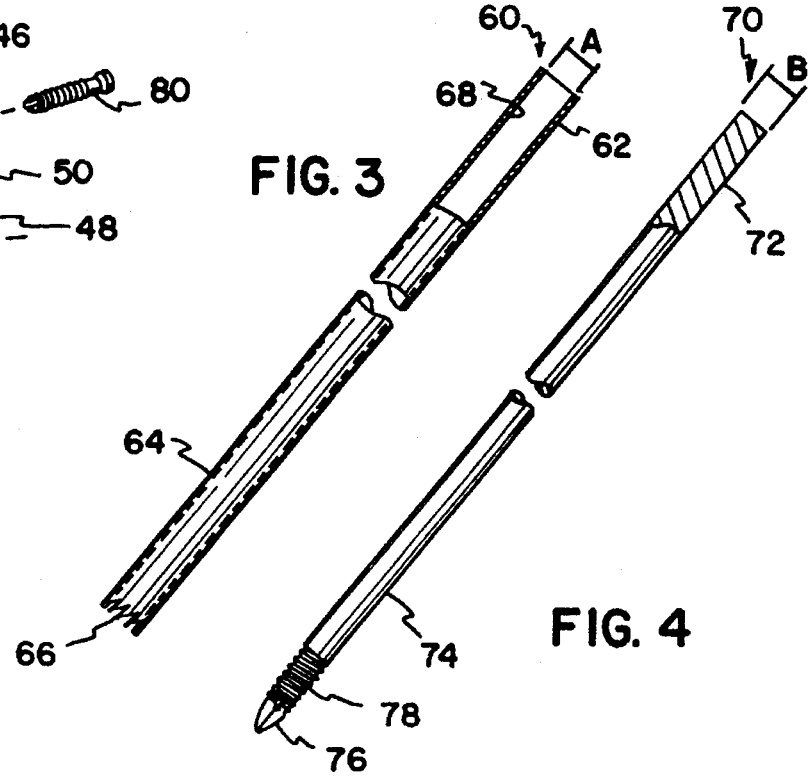
FIG. 4 is a view of an embodiment of a pin in partial cross-section, with a portion removed.

FIG. 4 shows a pin 70 including a first end 72 and a second end 74. Second end 74 is preferably provided with a pointed tip 76 and threads 78. Pin has a maximum outside diameter represented by dimension B. Pin may be inserted into the bone by applying a rotational force to pin 70 about its longitudinal axis, and an axial force. FIGS. 13B and C show pin 70 inserted into the bone 150, for example. Pin 70 may be constructed from any of a variety of medically approved materials. One preferred material is metal, such as stainless steel.

Figure 5:
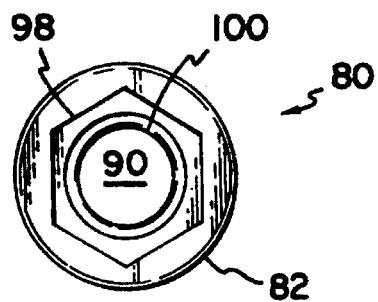
FIG. 5 is a head end view of an embodiment of a screw.
Figure 6:
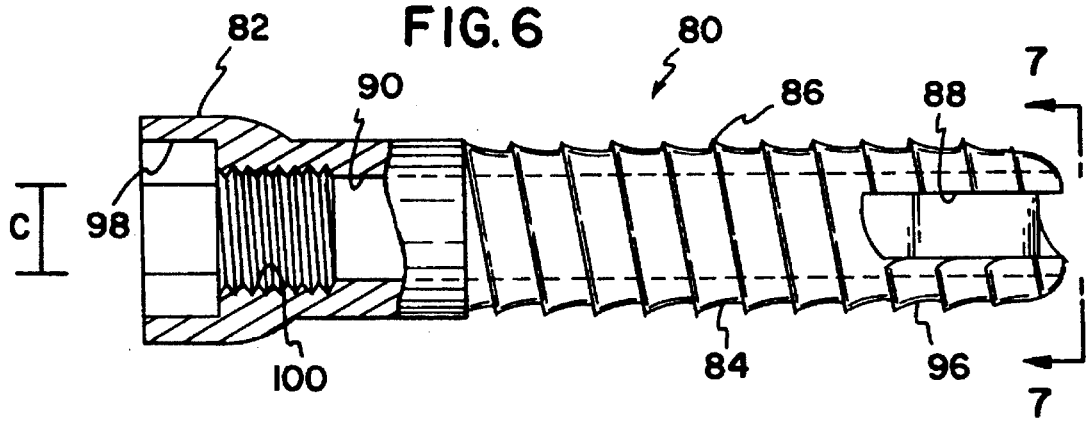
FIG. 6 is a side view of the screw shown in FIG. 5, in partial cross-section.
Figure 7:
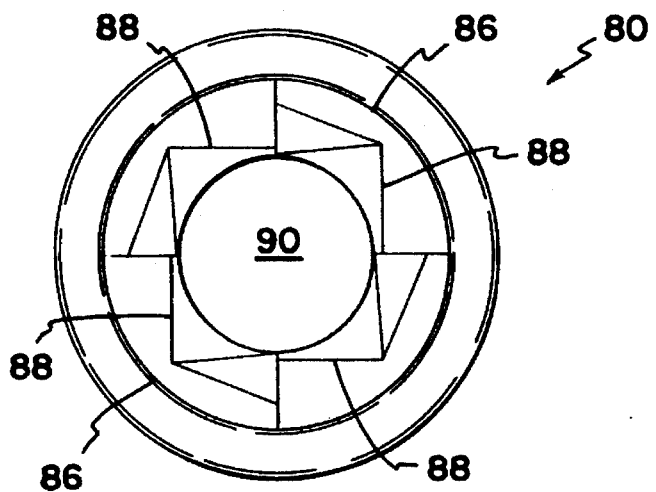
FIG. 7 is an enlarged tip end view of the screw shown in FIG. 5.
Figure 6A:
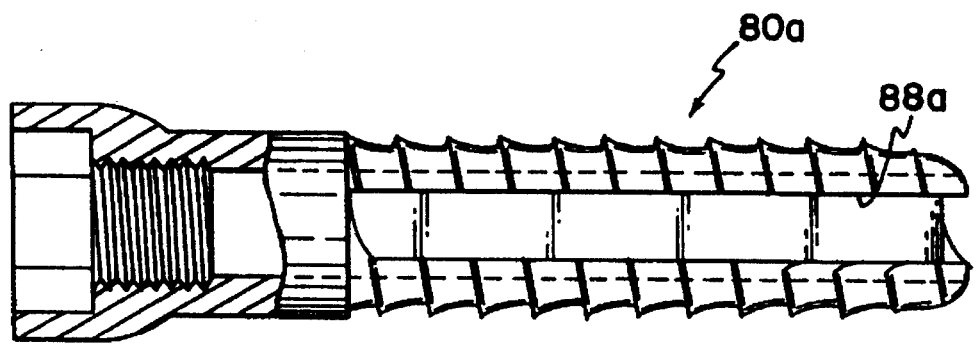
FIG. 6A is a side view of an alternative screw to the screw shown in FIG. 6.

Referring now to FIGS. 5–7, a screw 80 is shown having a head 82 and a shaft 84 with threads 86. Cutting flutes 88 are also provided in one preferred embodiment. The cutting flutes may extend for a greater distance toward head 82 than the length shown in FIG. 6. They may extend for nearly or fully the length of threads 86. In the embodiment of screw 80a of FIG. 6A, the flutes 88a continue for the length of the screw, creating a void through which marrow may be harvested. Referring again to FIG. 6, an interior passage 90 is defined through screw from first end 94 to second end 96. The minimum inside diameter of the interior passage 90 is represented as dimension C. Screw 80 may be made from a variety of medically approved materials. One useful material is metal, such as stainless steel.

Figure 13C:
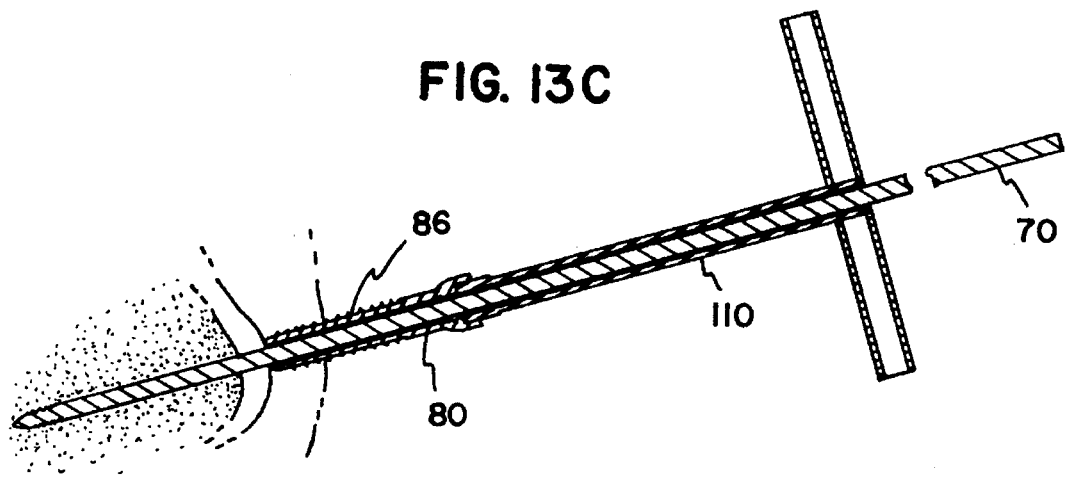
Figure 13D:
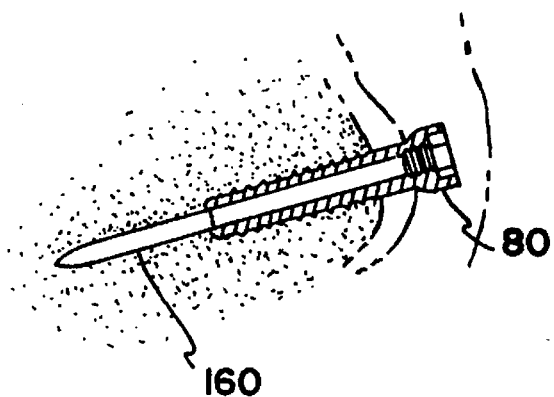

Screw 80 includes a hex-shaped interior portion 98 to facilitate turning of the screw with an appropriately shaped tool. Various other head designs are possible which permit engagement with a tool to facilitate turning of the screw about its longitudinal axis, and also the application of an axial force in the direction of the longitudinal axis. FIG. 13D shows screw 80 operatively positioned in bone 150.

Figure 13E:
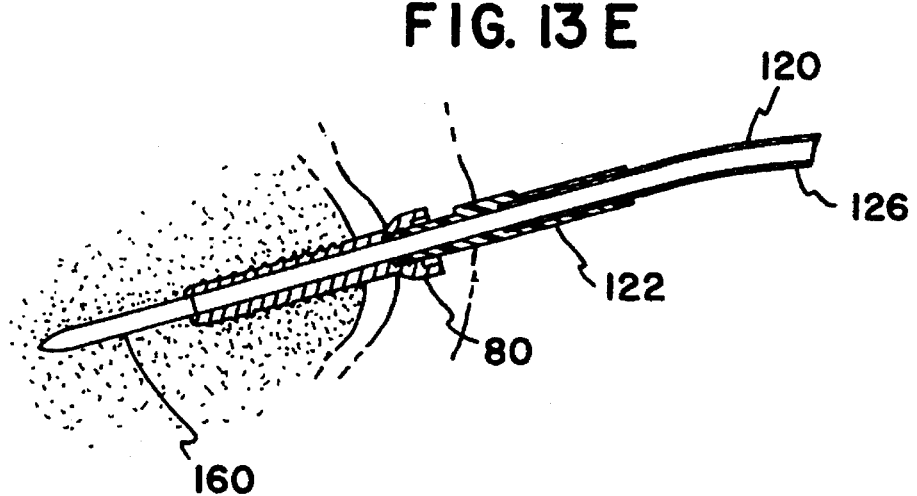

Screw 80 also includes structure on first end 94 permitting attachment to a fitting. One preferred structure includes inner threads 100. Pressure fittings and twist-lock fittings are also possible. Such alternative structures and others must provide a sufficient seal to permit bone marrow harvesting. FIG. 13E shows screw 80 attached to a tubing apparatus 120, for example.

Figure 8:
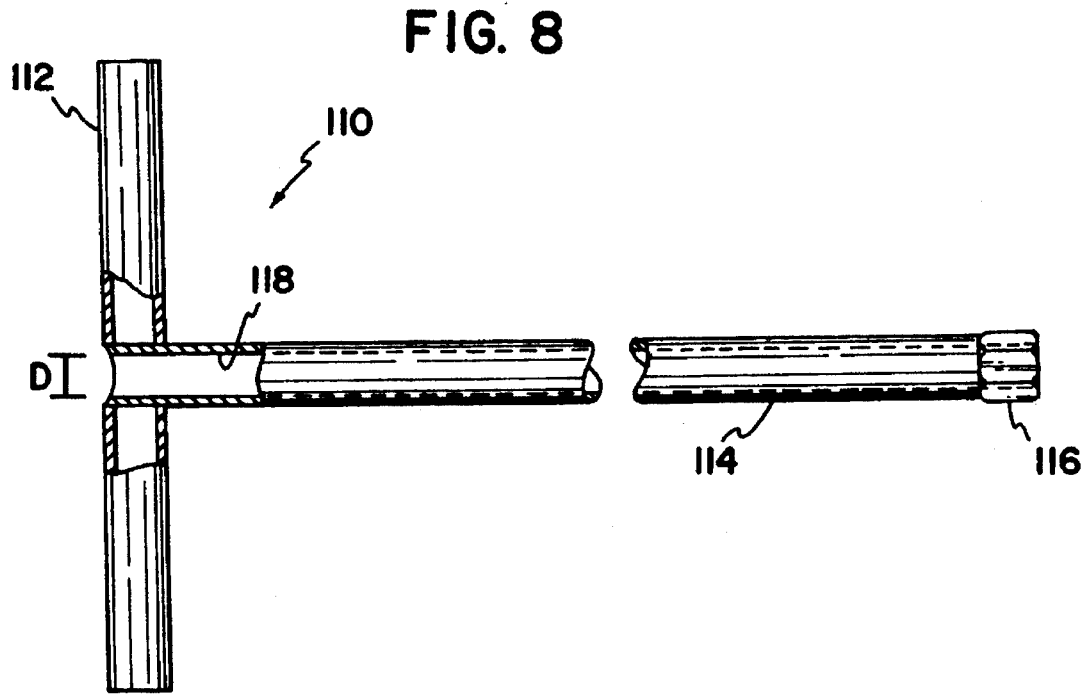
FIG. 8 is a view of an embodiment of a wrench in partial cross-section, with a portion removed.
Figure 9:
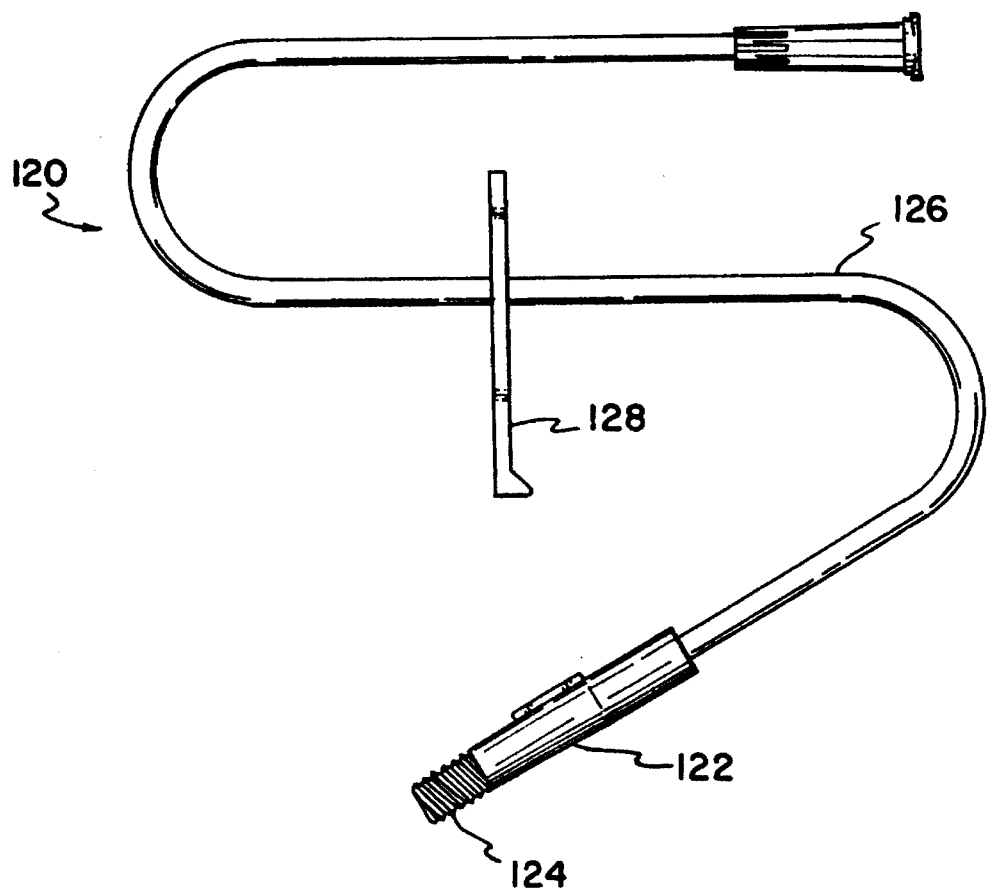
FIG. 9 is a view of a fitting and tubing.

A wrench 110, as shown in FIG. 8, is provided to turn screw 80. Wrench 110 includes a handle 112 and a shaft 114 which terminates in a hex-shaped tip 116. The hex-shaped tip is sized to fit the hex-shaped interior portion 98 on screw 80. Wrench 110 is further provided with an inner passage 118 having a minimum inner diameter defined by dimension D, for receiving pin 70. FIG. 13C shows wrench 110 in use, for example. The physician or other user applies rotational movement to handle 112 to turn screw 80 into or out of the bone. Wrench 110 may be constructed from any of a variety of materials. One preferred material is metal. Power instruments may also be used to insert the threaded devices.

Tubing apparatus 120 includes a fitting 122 with a first end 124 which sealably attaches to screw 80 during operation. A flexible plastic tubing 126 extends from fitting 122 to permit transport of bone marrow through tubing 126 to a distal end collection site. Negative pressure structure (not shown) is provided to create a vacuum or negative pressure environment inside of tubing 126. A fitting 122 made from rigid plastic is useful in the present invention. A clamp, such as a sliding tube clamp, may be provided in some cases.

Referring now to FIGS. 13A–F, methods of operation are shown. First, as shown in FIG. 13A, cannula 60 is inserted through the layers of tissue and skin 152 covering bone 150. Teeth 66 on cannula 60 engage bone surface 154.

Next, as shown in FIG. 13B, pin 70 is inserted into bone 150 through bone surface 154 wherein the pointed tip 76 extends into the interior of the bone 156. One method of inserting pin 70 into bone is to rotate pin 70, thereby permitting threads 78 to draw the pin into the bone. An axial force in the longitudinal direction is applied in addition to or alternatively to the rotational force.

Once pin 70 is inserted into bone 150, screw 80 is positioned on pin as shown in FIG. 13C. FIG. 13C shows wrench 110 in position to turn screw 80 into bone 150. Preferably, threads 86 draw screw 80 into bone 150. Cutting flutes 88 described above further cut into bone 150 as screw 80 is rotated, creating an open space adjacent the lateral side portions of screw 80.

A next step of one method according to the present invention is to remove wrench 110 from engagement with screw 80. Next, pin 70 is removed from the bone 150 and from screw 80. FIG. 13D shows the screw 80 operatively positioned in bone 150. Removal of pin 70 leaves void 160, which is believed to subsequently fill with bone marrow. As shown in FIG. 13D, it is preferable, but not required, to insert pin 70 into bone 150 at a greater depth than screw 80, for this reason. The void 160 is believed to facilitate more efficient bone marrow harvesting. Other tools besides wrench 110 can be used to rotate screw 80.

Next, tubing apparatus 120 is attached to screw 80 with fitting 122, as shown in FIG. 13E. A negative pressure is applied to tubing 126, which causes bone marrow to be withdrawn through screw 80 into tubing 126. Other fittings and connecting structures are anticipated, including Luer fittings and friction fittings, for example.

It is believed the present invention shown by FIGS. 13A–F is advantageous over prior systems since bone marrow is being withdrawn from various voids created in inside the bone in accordance with the present invention. For example, as shown in FIG. 13E, a first void 160 is created by pin 70. Second void regions are created by the cutting flutes 88 on screw 80. The cutting flutes 80 are believed to form an open channel adjacent to the lateral side portions of the screw for the passage of bone marrow toward the open end of the screw. The channel created by the cutting flutes 88 is continuous with the empty channel where pin 70 had been. These spaces create a large reservoir from which bone marrow can be removed by negative pressure. The reservoir is created because the membranes and bony spicules which enclose the marrow are broken down by the passage of the pin and the cutting flutes. This releases the marrow into the system.

The prior system of inserting a tube into the patient and then applying negative pressure to the tube typically produces an insufficient amount of marrow, because the volume of bone interior exposed to the negative pressure is small, roughly equal to the inner diameter of the tube which was inserted into the bone.

The delivery of marrow through the collecting device is facilitated in the present invention if the interspaces between bone spicules are opened up and exposed to the negative pressure of the device. The known system of inserting a plain tube or cannula into the bone is believed to not expose enough of the marrow to the negative pressure of the device. The present invention breaks down spicules to release the bone marrow. Typically, bone marrow rests inside of the bone in a liquid or semisolid state within cavities beneath the shell of the outer bone. With the prior system of the plain cannula, bone or bone fragments may block the entrance to the cannula. Reinsertion may be required. The present invention allows more of the cavities of bone marrow to be exposed to the negative pressure so that the bone marrow can be withdrawn. Bone fragments cannot easily block the opening to the screw. Further, the present invention is safer, since the pin and screw are inserted under control with gentle twisting movements.

Figure 13F:
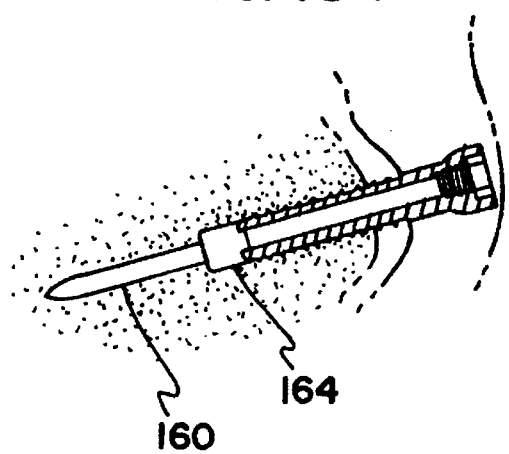

A further step in the method in accordance with the present invention is to withdraw the screw 80 slightly by rotating in the reverse direction. Withdrawing the screw creates a third void 164 as shown in FIG. 13F. In some cases, this step may further increase bone marrow flow through screw 80.

Figure 10:
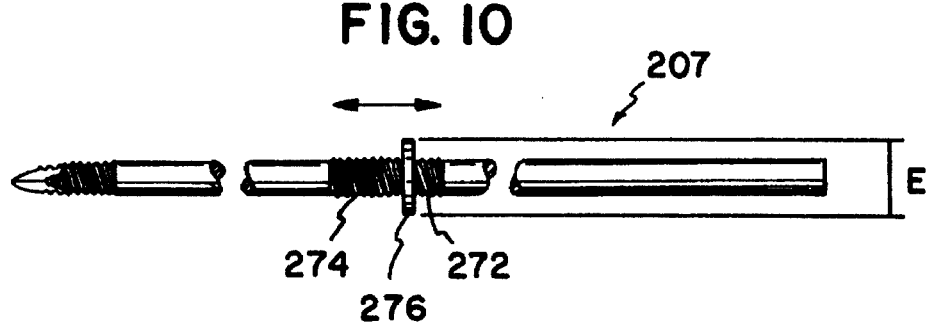
FIG. 10 is a view of a first alternative pin, with portions removed.

Various alternative embodiments and methods are possible in accordance with the present invention. FIG. 10 shows an alternative pin 270. In middle region 272, threads 274 are provided for engaging threads on nut 276. Nut 276 acts as a stop for limiting the amount of insertion of pin 270 into bone 150. Nut 276 provides pin 270 with a maximum outside diameter, dimension E, greater than the inside diameter 68 of cannula 60. The engagement of nut 276 on first end 62 of cannula 60 stops pin 270 from further insertion into bone 150. The position of nut 276 is variable on pin 270 by threadably moving the nut along the longitudinal axis of pin 270 to the desired position.

Once pin 270 is inserted to the proper depth, the nut 276 engages first end 62 of cannula 60. Nut 276 is then removed by threading nut 276 off pin 270. This permits cannula 60 to be removed from engagement with the bone once pin 270 is operatively inserted into the bone.

Figure 11:
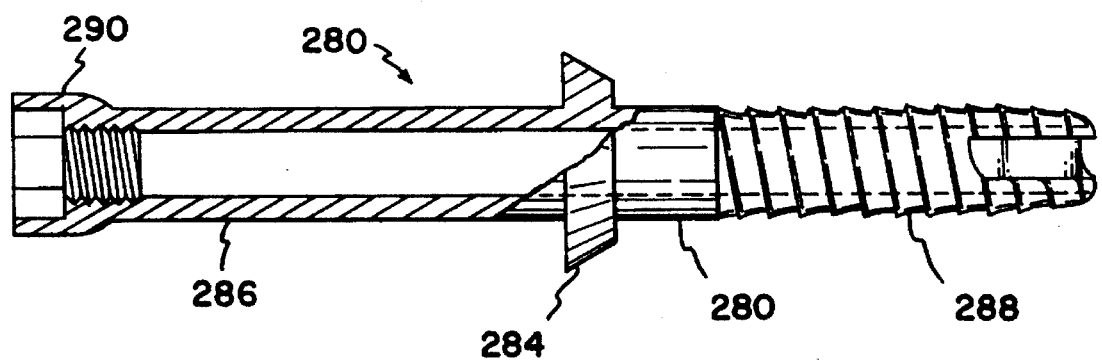
FIG. 11 is a view of a first alternative screw in partial cross-section.

FIG. 11 shows an alternative embodiment of screw 280. Screw 280 is elongated from screw 80. In middle region 282, a bone stop 284 is provided to engage bone surface 154. Extension region 286 extends from stop 284. Extension region 286 may facilitate easier harvesting by distancing the fitting portion 290 of screw 280 away from the bone and the tissue surrounding the bone. It is to be appreciated that extension region 286 could be a separate piece from stop 284 and shaft 288. Threads, for example, could attach the two structures together.

Alternative bone stops 292, 294, 296 to bone stop 280 are shown in FIGS. 11A–C.

Figure 12:
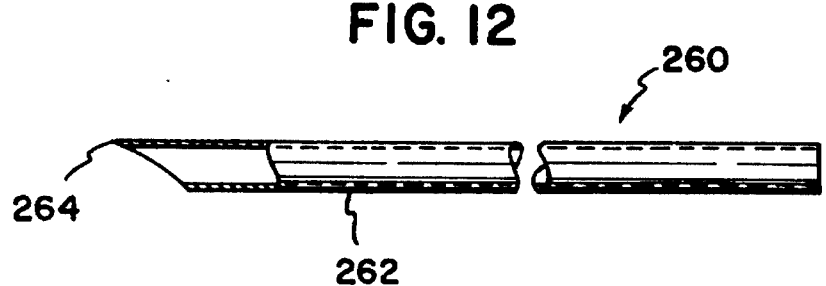
FIG. 12 is a view of a first alternative cannula in partial cross-section, with a portion removed.

FIG. 12 shows an alternative embodiment of a cannula 260. On end 262 of cannula 260, a single needle-like point 264 is formed, instead of a plurality of teeth 66 as in cannula 60. Needle point 264 digs into the bone to prevent sliding of cannula 260 relative to the bone during insertion of pin 70 or pin 270.

FIG. 14 shows an additional embodiment of a pin 300. Pin 300 has a first portion 302 for insertion into the bone. An enlarged portion 304 is sized to remain outside of the bone. At least a part of enlarged portion 304 may be below the outside surface of the skin. Portion 304 is sufficiently long to extend beyond the outer reaches of the skin to permit easy grasping by the physician. Stop surface 306 is formed at the interconnection region between first portion 302 and second portion 304. Stop surface 306 acts as a stop to limit the amount of axial insertion of pin 300 into the bone.

It is anticipated that pin 300 is useable without a guide cannula like cannula 60, 260. However, a cannula could be used as long as the cannula is large enough to accept enlarged second portion 304. Pin 300 is used to provide a guide structure for the screw that is threaded into the bone. The screw would require an inner passage having a diameter at least as great as enlarged portion 304.

Figure 14A:
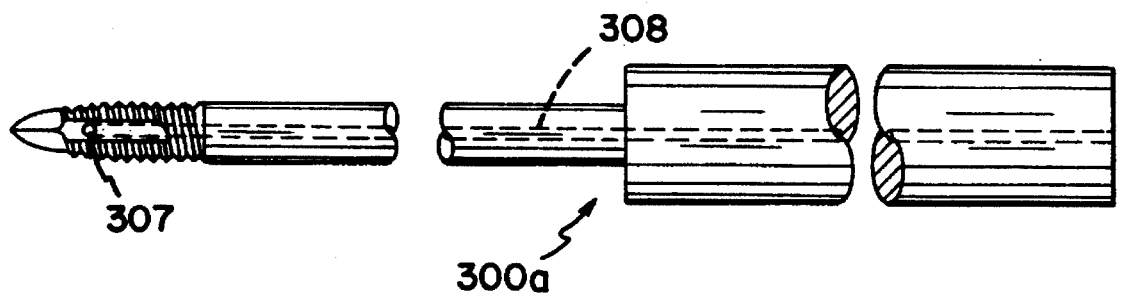
FIG. 14A is an alternative pin to the pin of FIG. 14, including a hollow passage and flutes.

Referring now to FIG. 14A, pin 300a is provided with a flute 307 for forming a recess for bone marrow collection. Passage 308 is provided for connections to a vacuum source. Pin 300a functions much like screw 80 and its various alternatives.

Figure 15:
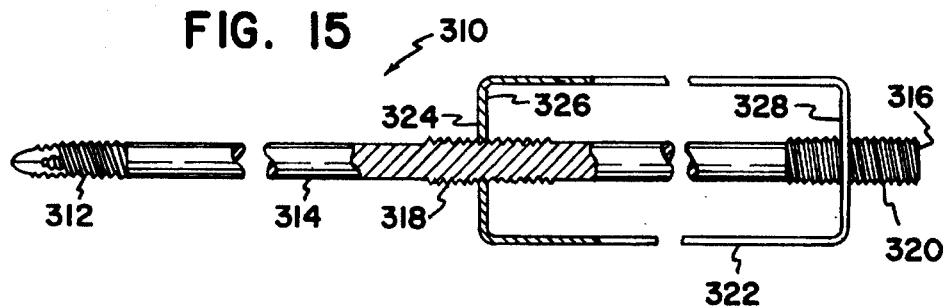
FIG. 15 is a view of a third alternative pin, with portions removed, and with portions shown in cross-section.

Referring now to FIG. 15, pin 310 is shown. It is anticipated that pin 310 can be used with or without a guide cannula such as cannula 60 or cannula 260, as described previously. Pin 310 includes a tip 312 for insertion into the bone. Pin 310 further includes a first threaded region 318 and a second threaded region 320. First threaded region 318 is located adjacent a middle portion 314 of pin 310. Second threaded region 320 is located on an end 316 of pin 310. A stop arrangement 322 is threadably mounted to pin 310. In FIG. 15, stop arrangement 322 is shown in a cross-sectional view.

One possible shape of stop arrangement 322 is cylindrical. The stop arrangement 322 includes a stop surface 324 for engaging the outer surface of the bone or the end of the cannula. Stop surface 324 limits the amount of axial insertion of pin 310 into the bone. Stop arrangement 322 is mounted to pin 310 via threaded end 326 and threaded end 328. The threads on the threaded ends 326, 328 are provided with the same pitch such that rotation of stop arrangement 322 about the longitudinal axis relative to pin 310 will move the stop arrangement 322 either toward tip 312 or away from tip 312. In this manner, adjustability of the stop surface 324 relative to tip 312 is provided.

Second threaded portion 320 may have an identical thread height with first threaded portion 318. In some instances, although, not required, a different height may be provided to mate with the appropriate threaded end 326, 328 such that the first threaded end 326 passes freely over second threaded region 320 when stop arrangement 322 is attached or removed from pin 310.

Figure 16:
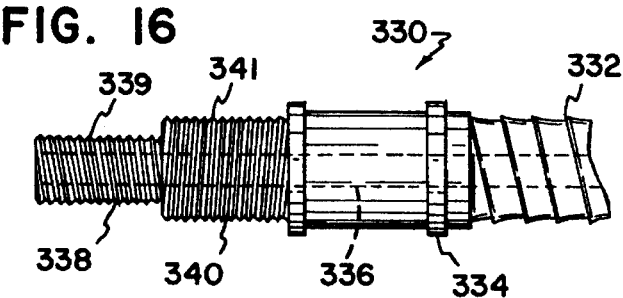
FIG. 16 is a view of a portion of a fifth alternative screw.

FIG. 16 illustrates a further alternative embodiment of a screw 330. Screw 330 includes a threaded first end 332 for engaging the bone. Stop 334 acts to limit the amount of insertion of screw 330 into the bone. A hollow bore 336 extends through the screw from one end of the screw which is exposed from the bone down to the region in the screw having threads 332. As will be discussed below, hollow bore 336 may extend completely from one end of the screw to the other. Alternatively, hollow bore 336 may include one or more side ports which extend from the axial bore outwardly in a radial direction, with or without the bore extending all the way to the tip region at the end with threads 332. Bore 336 is utilized to harvest bone marrow.

Screw 330 is provided with structure for engaging a particular tool arrangement for insertion of the screw 330 into the bone. Also, screw 330 includes structure for engaging a different tool arrangement to permit rotation of the screw out of the bone. A first threaded end 338 on screw 330 includes threads 339 having a regular or conventional screw thread direction. A second threaded region 340 includes threads 341 which are a reverse direction to threads 339. Further, threads 341 include an outside diameter greater than the threads 339. By providing two separate tools, or a single tool with dual thread-engaging structures, the tool or tools can be threadably attached to screw 330 for insertion, and later removal of the screw relative to the bone.

Figure 17:
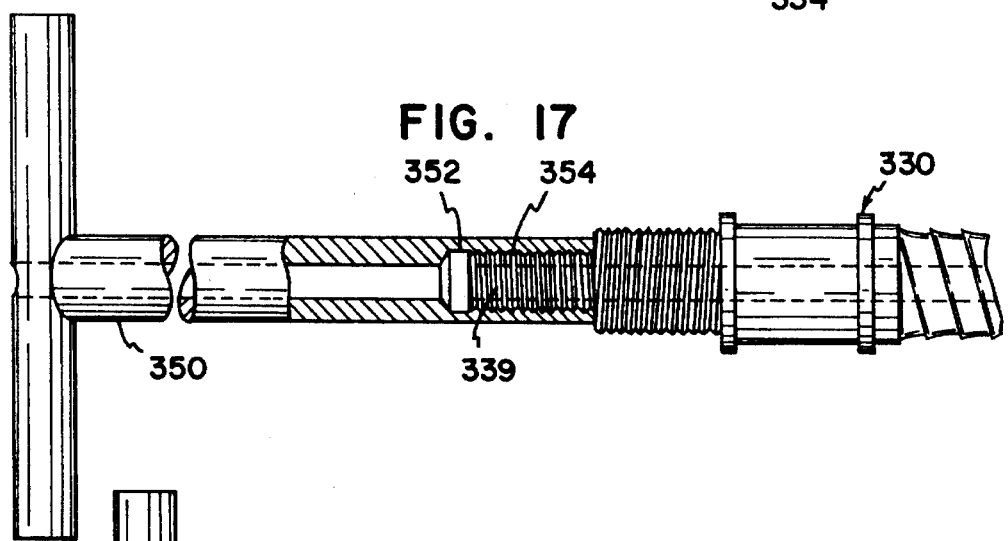
FIG. 17 is a view in partial cross-section, with portions removed, showing a first threaded wrench to rotate the fifth alternative screw into the bone.

For example, in FIG. 17, a first threaded wrench 350 includes a bore 352 for receiving first end 338 of screw 330. Threads 354 on bore 352 of wrench 350 engage threads 339 on screw 330. To insert screw 330 into the bone, wrench 350 is threadably secured onto threads 339. Once further tightening is no longer possible, wrench 350 is able to transmit rotational movement applied to the handle of wrench 350 to screw 330 to insert screw 330 into the bone. To remove the wrench 350, wrench 350 is rotated in the reverse direction, leaving screw 330 in the bone. Bore 356 through wrench 350 accommodates a guide pin if such guide pin is present. Bore 356 is not needed if no guide pin is used.

Figure 18:
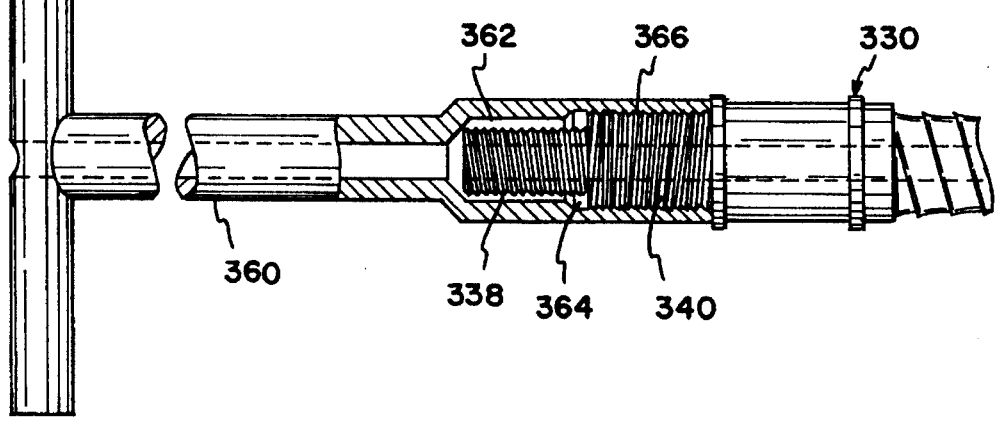
FIG. 18 is a view in partial cross-section, with portions removed, showing a second threaded wrench to rotate the fifth alternative screw out of the bone.

Referring now to FIG. 18, a second threaded wrench 360 is provided for the purposes of removing screw 330 from the bone. First wrench 350 would not easily be usable since rotation of wrench 350 would not readily transmit force through to screw 330. Instead, first wrench 350 would likely separate from screw 330 if wrench 350 was rotated in a direction to remove the bone screw 330. In particular, rotation of first wrench 350 in this direction is specifically intended to separate screw 330 from wrench 350 to permit bone marrow harvesting through screw 330.

Second wrench 360 includes a first bore 362 for freely receiving first end 338. Wrench 360 includes a second bore 364 with a larger bore diameter for receiving second portion 340 of screw 330. Bore 364 includes threads 366 for engaging threads 341 on second portion 340 of screw 330.

Second wrench 360 is threadably attached to screw 330 by rotating wrench 360 in an opposite direction to the direction to attach wrench 350 to screw 330. Once further rotation is not permitted, wrench 360 is in a position to transmit rotational movement of wrench 360 to screw 330 to remove the screw from the bone. To later separate wrench 360 from screw 330, wrench 360 is rotated in the reverse direction relative to screw 330.

It is to be appreciated that threads 339 and threads 341 could be switched in terms of location. If switched, threads 339 would need to be provided with a larger diameter than threads 341.

Figure 19:
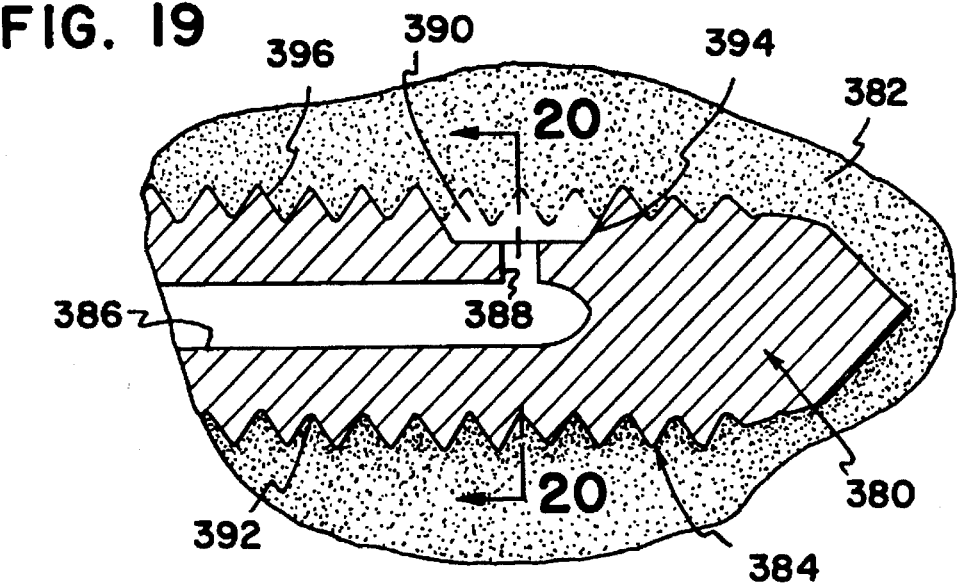
FIG. 19 is a cross-sectional view of a portion of a sixth alternative screw, showing the portion of the screw operatively positioned in the bone.

Referring now to FIG. 19, an alternative screw 380 is shown. Screw 380 is positioned in bone 382. Threads 384 on an outside surface of screw 380 engage the bone 382. A bore 386 permits removal of bone marrow from the bone through screw 380. A side port 388 extends in a radial direction from bore 386 relative to screw 380. Side port 388 is useful to evacuate bone marrow from adjacent a side of screw 380. Screw 380 is further provided with a portion of missing threads, or removed threads in a region adjacent bore 386. The threads may be removed by grinding, machining, or other known material removal processes. Alternatively, the screw may be manufactured with the missing threads in this area.

The missing thread area defines a discontinuous threaded region since the threads do not uniformly maintain their height, width, or overall profile as the threads travel about the longitudinal axis of the screw. Further, a portion of shaft 392 of screw 380 may also be provided with a indented area, or a portion physically removed if previously provided. The result of not providing a portion of threads, or removing the threads, and possibly a portion of shaft 392 adjacent side port 388 is that a void 390 is created adjacent screw 380 when the screw is operatively positioned in the bone. The void is believed to fill with bone marrow such that bone marrow may be more easily withdrawn from the bone. The region or void created by the threads previously inserted into the bone is represented by void region 390. In void 390, more bone interior is exposed to the vacuum source, than if the side port exited screw 380 at the surface of a thread or at a place on the core not positioned adjacent any void. It is to be appreciated that the threads may be removed fully as shown or only partially removed to create the desired voids. Cutting flutes at the tip of screw 380 may be provided extending toward and communicating with side port 388.

In some instances, it may be desirable to provide different-sized threads on screw 380 to ensure a that proper vacuum is created. For example, threaded portion 394 which creates the voids 390 are typically provided with a first height. Threaded portion 396 on a second region of screw 380 may be provided with a larger height to help seal void region 390 from access to the exterior of the bone.

Figure 20:
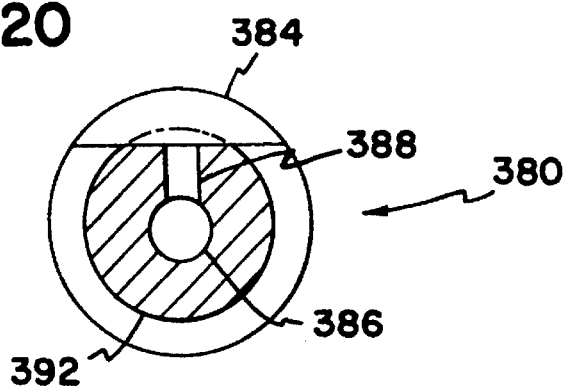
FIG. 20 is a cross-sectional end view of the screw shown in FIG. 19 along lines 20—20.
Figure 21:
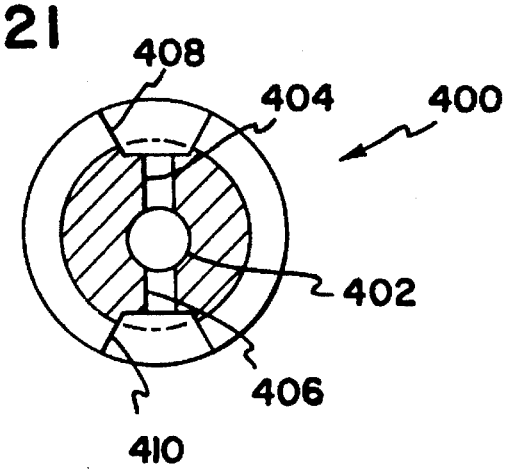
FIG. 21 is a cross-sectional end view of a modified screw to the screw shown in FIGS. 19 and 20.

FIG. 21 illustrates an alternative embodiment of screw 400 to the screw 380 shown in FIGS. 19 and 20. Screw 400 includes an axial bore 402 like axial bore 386. Two side ports 404 and 406, on opposite sides are provided to communicate with the bone from axial bore 402. The side ports exit in direct opposite directions at the same point on the longitudinal axis. Cutouts 408 and 410 are associated with respective side ports 404 and 406. It is to be appreciated that cutouts 408,410 can be one thread long or may extend for more than one thread. Also, the arc length of the cutouts can be smaller or larger than that shown in FIG. 21. Deeper or shallower cutouts may be provided. These cutout areas define discontinuous threaded regions since the threads do not uniformly maintain their shape as the threads travel about the longitudinal axis of the screw. In particular, a portion of the entire thread and a portion of the shaft is completely missing. Cutouts 408,410 may be machined out or the screw 400 may be formed to include the cutouts.

It is to be appreciated that at least some thread is desireable in a 360° span around screw 400 such that removal of the screw is better facilitated. In some cases, there may be only a small region in the bone which securely engages the threads. If such region is at some point not engaged by any threads, the screw may not be operatively engaged with the bone such that rotation would not easily, or fail to, turn the screw and advance the screw from the bone.

In some further modifications anticipated for screws 380, 400, the missing thread portions, or cutouts may extend for one or more threads lengths. If more than one side port location is provided at spaced apart locations along the longitudinal axis of the screw, the side ports may be all facing in the same direction, or they may be offset from each adjacent to face in different directions as the axial bore extends along the longitudinal axis.

Figure 22:
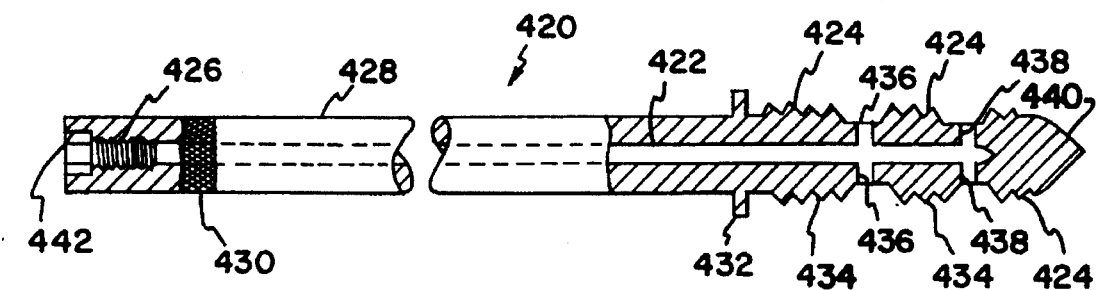
FIG. 22 is a view of a seventh alternative screw, with portions shown in cross-section, and with portions removed.

FIG. 22 shows an alternative screw 420. Screw 420 includes an axial bore 422 which extends from a first end 428 to a tip 440. It is noted that axial bore 422 does not exit tip 440 parallel to the longitudinal axis. Instead, bore 422 exits from the screw at a plurality of side ports 436,438. Similar structure is shown in FIGS. 19–21. Screw 420 includes threads 426 for engaging connecting structure for connecting screw 420 to a vacuum source.

As shown in FIG. 22, adjacent the side ports 436,438 are missing threads. These areas define discontinuous threaded regions since the threads do not uniformly maintain their height, width, or overall profile as the threads travel about the longitudinal axis of the screw. It is preferred that the discontinuous threaded regions are not discontinuous for a full 360 degrees about the longitudinal axis. Some preferred structures are seen in FIGS. 20 and 21 with respect to the span of the discontinuous threaded regions relative to the longitudinal axis.

Screw 420 may be useful in that screw 420 can be turned directly into the bone without the use of a guide pin. Screw 420 can be inserted directly into a surgical drill wherein the drill grips screw 420 at drill-engaging surface 430. During rotation of screw 420, tip 440 provides both self-drilling and self-tapping of screw 420 such that screw 420 is rotatably and axially inserted into the bone. A self-drilling tip means no pre-drilled or preformed guide hole is needed. A self-tapping tip means no separate tap is necessary to form the internal threads in the bone to be engaged by threads 384.

On screw 420, stop 432 limits the amount of axial insertion of the screw 420 into the bone. End 428 extends sufficiently away from stop 432 such that threads 426 are easily accessible and are not interfered with by skin or other tissue surrounding the bone.

Screw 420 includes threaded portion 424 having a first height. Second threaded portion 434 may be provided with a larger height to seal the side ports 436,438 from the opening into the bone.

Hex head 442 can be utilized to turn screw 420 in either direction, either into the bone or out of the bone by providing an appropriately shaped wrench.

Figure 23:
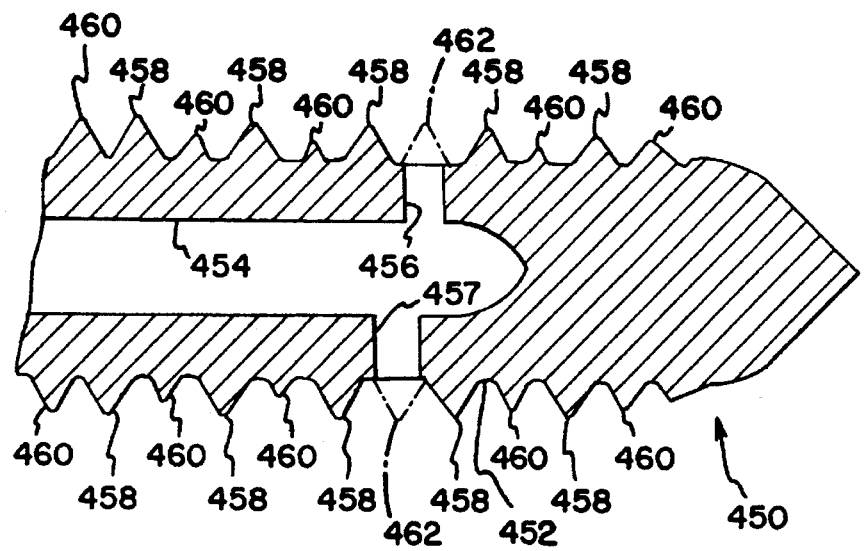
FIG. 23 is a cross-sectional view of a portion of an eighth alternative screw.

Referring now to FIG. 23, screw 450 is shown. Screw 450 includes a core 452 defining a shaft of the screw. Axial bore 454 passes through an interior of screw 450. Axial bore 454 exits screw 450 at side ports 456,457. These side ports permit bone marrow to enter axial bore 454 from the bone. Core 452 includes first threads 458 extending along the screw 450. Second thread 460 is equally spaced between the threads of first threads 458. Second thread 460 tapers out and in along screw 450. Where second thread 460 is missing, a convenient location for side portions 456,457 is provided. During insertion of screw 450, second thread 460 cuts through the bone to leave a void region 462 in the area where second thread is missing once screw 450 is operatively positioned. This void is adjacent side portions 456,457 for withdrawing bone marrow from the bone. Second thread 460 is a discontinuous threaded portion with respect to screw 450.

Once screw 80 or any of the other embodiments is operatively positioned in the bone, the axial bore 90 provides a convenient access port for accessing the interior of the bone. Such access is useful for harvesting the bone marrow, as described above. Such access may also be useful for measuring intraosseous pressure in the bone, or administering systemic medication.

Figure 24:
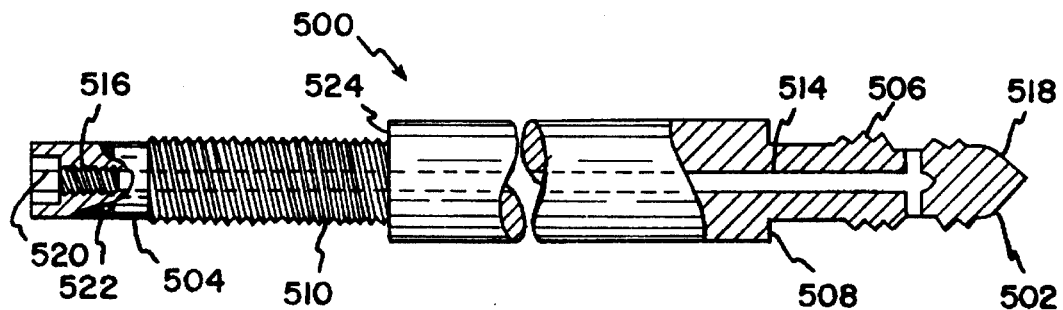
FIG. 24 is a view of an eighth alternative screw, with portions shown in cross-section, and with portions removed, for use in a bone biopsy.

Referring now to FIGS. 24, 25, and 26A–C, systems and methods are shown for bone biopsy procedures. In FIG. 24, a screw 500 is shown having a first end 502 for insertion into the bone, and a second end 504 which protrudes from the bone during use. Threads 506 are provided to threadably engage the bone during rotation of screw 500 into the bone. Screw 500 includes a stop 508 for limiting the amount of insertion of screw 500 into the bone. Adjacent second end 504 of screw 500 are threads 510 to engage threads on a cannula. Screw 500 optionally includes an internal bore 514 and internal threads 516 which are useful in bone marrow harvesting should screw 500 also be used for that purpose. Screw 500 includes a self-drilling and self-tapping tip 518 which permits insertion of screw 500 into the bone upon the application of rotational motion and an axial force to screw 500. Screw 500 includes a scored portion 522 to permit easy gripping of the screw by drill or other tool or by hand in order to rotate screw 500 into the bone. Screw 500 further includes an internal hexagonal head 520 to permit rotation of screw 500 with the appropriately shaped tool. Alternatively, a slotted head may be provided instead of internal hexagonal head 520.

Figure 25:
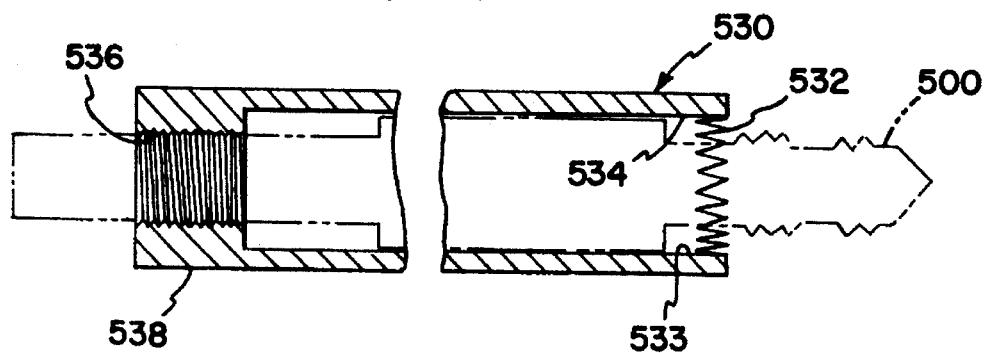
FIG. 25 is a view of a cannula used in connection with the screw of FIG. 24 in a bone biopsy.

Referring now to FIG. 25, a cannula 530 is shown with teeth 532 for engaging the bone. Cannula 530 includes an inside surface 533 defining a bore 534. Bore 534 is sufficiently large to receive the first end 502 and second end 504 of screw 500 of FIG. 24. Cannula 530 is provided with internal threads 536 which are engageable with second threads 510 of screw 500. Cannula 530 further includes a scored exterior gripping surface 538 to permit easy gripping of cannula 530. There is sufficient clearance inside cannula 530 such that cannula 530 can slideably receive screw 500. Too much clearance should be avoided so that cannula 530 is securely and accurately guided into the bone around screw 500 as will be discussed below in greater detail.

Figure 26A:
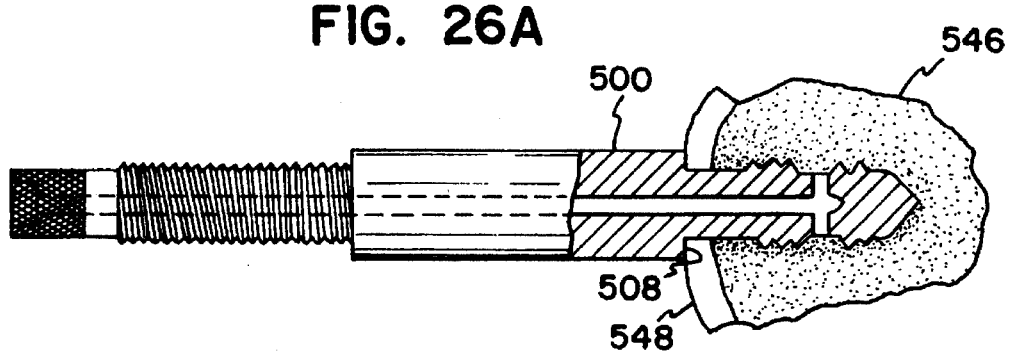
FIGS. 26A–C illustrate various steps in one method according to the present invention for gathering a bone core in during the bone biopsy.
Figure 26B:
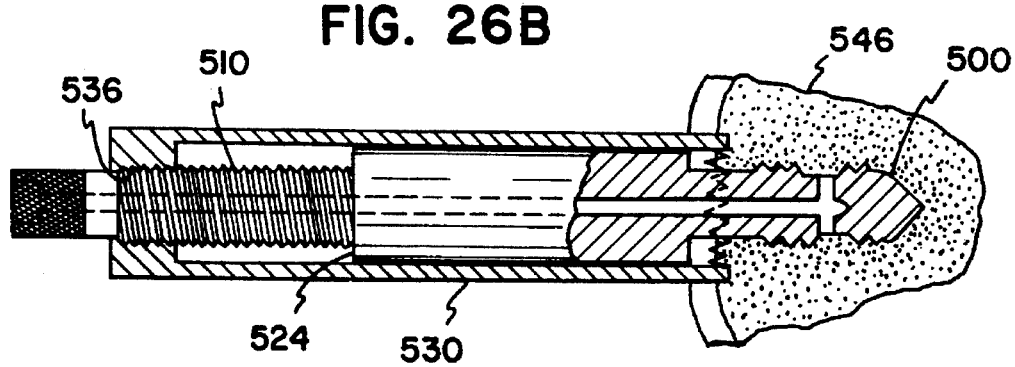
Figure 26C:
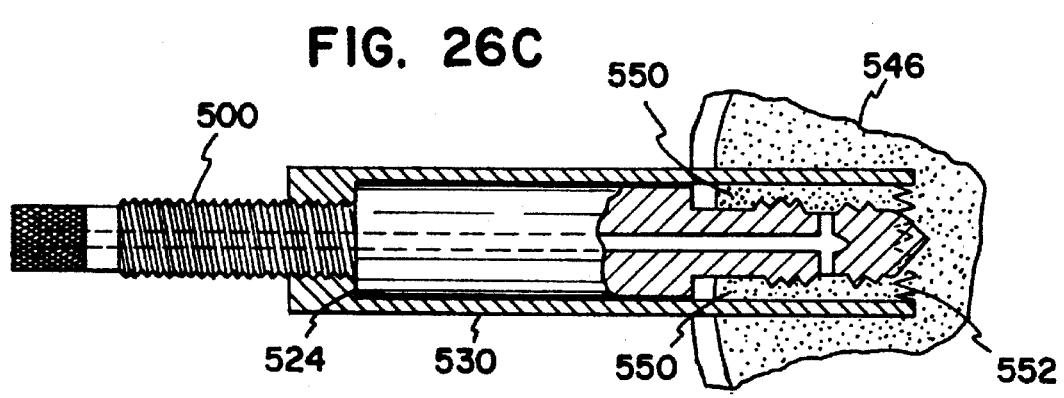

Referring now to FIGS. 26A–C, a bone marrow biopsy procedure according to the present invention is illustrated. In FIG. 26A, screw 500 is shown positioned in bone 546. As shown in FIG. 26A, stop surface 508 of screw 500 engages exterior surface 548 of bone 546. Screw 500 has been positioned in bone 546 by the application of an axial force and a rotational motion to screw 500. Once screw 500 is operatively positioned in bone 546, cannula 530 is slidably positioned over screw 500 as shown in FIG. 26B. Also shown in FIG. 26B is the partial positioning of an end of cannula 530 into bone 546. It is believed preferable that cannula 530 engage bone 546 before threads 536 of cannula 530 engage second threads 510 of screw 500. Once threads 536 of cannula 530 engage second threads 510 of screw 500, cannula 530 is rotated to move cannula 530 deeper into bone 546.

As shown in FIG. 26C, cannula 530 has been fully threaded onto screw 500 such that further rotation of cannula 530 transfers directly to screw 500. Surface 524 of screw 500 acts as a stop to limit further axial movement of cannula 530 toward bone 546. Upon the continued rotation of cannula 530, the bone positioned in bone chamber 550 between cannula 530 and screw 500 will snap off at region 552 such that a generally cylindrical hollow core of bone is separated from the remaining bone of bone 546. The cannula 530 and screw 500 are together removed from the bone and then cannula 530 is separated from screw 500, such as by utilizing the internal hexagonal head 520 of screw 500. The bone core 550 can be analyzed for various characteristics according to the bone biopsy procedures necessary for desired treatment, analysis, or diagnosis. The bone core is generally columnar in shape with a hollow interior. The outer shape of screw 500 and the structures associated with the bone may cause the core to have a variety of irregular shapes, but all generally resembling a hollow cylindrical column.

It is to be appreciated that screw 500 may initially be used for bone marrow harvesting, and then for a bone biopsy in accordance with methods of the present invention.

From the foregoing detailed description of the present invention, it has been shown how the objects of the invention have been obtained in a preferred manner. However, modifications and equivalents of the disclosed concepts, such as those which would readily occur to one skilled in the art, are intended to be included within the scope of the claims.

What is claimed is:

1. A method of harvesting bone marrow from a desired region of a bone, the bone having an exterior surface, the method comprising the steps of:
   a) providing a screw with an interior passage extending from a first end to a threaded second end;
   b) providing a pin having a first end and a second end, the second end of the pin being receivable in the interior passage of the screw;
   c) inserting the second end of the pin into the bone to a desired depth;
   d) positioning the screw on the pin by concentrically aligning the pin with the interior passage of the screw;
   e) moving the screw along the pin in a direction from the first end of the pin toward the second end of the pin and inserting the second end of the screw into the bone to a desired depth;
   f) removing the pin from the bone and from the interior passage of the screw; and
   g) removing bone marrow from the bone from the first end of the screw through the interior passage of the screw.

2. The method of claim 1, further comprising the steps of:
   a) providing a cannula;
   b) positioning the cannula around the screw;
   c) inserting one end of the cannula into the bone such that a chamber is defined between the second end of the screw and the one end of the cannula, wherein a generally cylindrical section of bone is positioned in the chamber;
   d) rotating the screw and the cannula relative to the bone until the cylindrical section of bone becomes separated from a remainder of the bone; and
   e) removing the screw, the cannula, and the cylindrical section of bone from the remainder of the bone.

3. The method of claim 1, wherein the step of inserting the second end of the pin into the bone to a desired depth includes inserting the second end of the pin into the bone to the desired depth which is greater than the desired depth of the screw.

4. The method of claim 1, further comprising the steps of:
   a) providing a cannula with an inner passage extending from a first end to a second end; and
   b) before the step of inserting the pin into the bone, positioning the second end of the cannula adjacent to the desired region of the bone on the exterior surface of the bone, and inserting the pin through the cannula prior to the pin being inserted into the bone.

5. The method of claim 1, further comprising the step of partially withdrawing the screw from the bone once the screw is inserted into the bone and removing bone marrow from the bone through the interior passage of the partially withdrawn screw.

6. The method of claim 1, further comprising the step of providing cutting flutes on the second end of the screw, and cutting the bone with the cutting flutes as the screw is inserted into the bone.

7. The method of claim 1, wherein the step of providing the screw includes providing the second end with a discontinuous threaded portion defined by a discontinuous thread, and further comprising the step of cutting the bone with the second end to leave a void adjacent the discontinuous threaded portion.

8. The method of claim 1, further comprising the steps of:
   a) providing a tubing having an interior, and seal means for sealing the tubing to the first end of the screw, the interior passage of the screw being in fluid communication with the interior of the tubing; and
   b) the step of removing bone marrow through the screw including the step of applying a negative pressure through the tubing, the negative pressure permitting removal of bone marrow from the bone-through the screw.

9. The method of claim 4, further comprising the steps of:
   a) providing the pin with a first portion having a maximum outer diameter smaller than the inner passage of the cannula, the pin further having a stop mechanism for selectively changing an outer diameter of a first portion of the pin in a desired location on the pin such that the diameter is initially greater than the inner passage of the cannula;
   b) inserting the pin into the bone until the stop mechanism engages the first end of the cannula; and
   c) reducing the diameter of the pin at the stop mechanism such that the cannula can be removed from the pin.

10. A bone marrow harvesting screw comprising:
    a) a head including;
       i) means for engaging a tool to permit turning of the screw by the tool; and
       ii) means for attaching the head to a negative pressure source; and
    b) a shaft defining a longitudinal axis, the shaft extending from the head and terminating in a tip, the shaft including:
       i) an outside surface including a threaded region with an outer diameter comprising a thread having a first thread section and a second thread section for engaging the bone, the first and second thread sections being part of the same thread, the outside surface including a discontinuous threaded region located at a point from the longitudinal axis in a radial direction closer than the outer diameter of the threaded region, the discontinuous threaded region disposed on the shaft such that the threaded region surrounds the discontinuous threaded region, the discontinuous threaded region being defined by a spacing of the first thread section from the second thread section;
       ii) an inner surface defining an interior passage from the head toward the tip; and
       iii) a side port connecting the interior passage to the discontinuous threaded region.

11. The screw of claim 10, further comprising flutes on the outside surface of the shaft.

12. The screw of claim 10, further comprising self-drilling means for drilling into a substrate and self-tapping means for cutting threads into the substrate associated with the tip.

13. The screw of claim 10, wherein first and second threads are provided on the threaded region, the first thread being continuous, the second thread being discontinuous to form the discontinuous threaded region.

14. The screw of claim 10, wherein the means for engaging a tool includes first threads having a first thread direction.

15. The screw of claim 14, wherein the means for engaging a tool includes second threads having a second direction opposite to the first direction of the first threads.

16. A bone marrow harvesting kit comprising:

a) a screw including:
   a head having means for engaging a tool to permit turning of the screw by the tool; and means for attaching the head to a negative pressure source; and
   a shaft extending from the head and terminating in a tip, the shaft having an outside surface including threads for engaging the bone; and an inner surface defining an interior passage from the head toward the tip;

b) a pin having a first end and a second end, the second end being insertable into the bone, the second end of the pin being receivable in the interior passage of the screw prior to inserting the screw into the bone, the second end of the pin being insertable into the bone prior to inserting the screw into the bone;

c) a cannula with an inner passage extending from a first end to a second end, the inner passage sized to receive the pin prior to inserting the pin into the bone, the cannula being removable from the pin prior to inserting the screw into the bone.

17. A method of bone marrow harvesting comprising the steps of:

a) providing a screw having an inner passage extending from a head toward a tip, the inner passage exiting the screw at a port, the tip being provided with self-drilling means for drilling into a substrate and self-tapping means for cutting threads into the substrate, the screw further being provided with threads located at a region between the tip and the head, wherein the port is a side port exiting the screw perpendicular to a longitudinal axis of the screw, and wherein the threads surround the side port, the screw further comprising means to form a void in the bone adjacent the side port;

b) rotating the screw into the bone to position the port in the bone interior, wherein the step of rotating the screw into the bone forms a void adjacent the side port with the means to form a void; and c) removing bone marrow from the head of the screw by applying suction to the head such that bone marrow is transported from the bone interior through the port to the inner passage and then to the head.

18. The method of claim 17, further comprising the steps:

a) attaching a cannula to the screw and inserting an end of the cannula into the bone to position a portion of the bone between the screw and the cannula;

b) rotating the screw and the cannula together relative to the bone to separate the bone portion from the rest of the bone.

19. A bone biopsy kit comprising:

a) a screw including:
   a head having means for engaging a tool to permit turning of the screw by the tool;
   a shaft extending from the head and terminating in a tip, the shaft having an outside surface including first threads for engaging the bone, a stop for engaging an exterior surface of the bone, the stop disposed on the shaft between the first threads and the head, and second threads disposed on the shaft between the stop and the head; and b) a cannula with an inside surface defining an inner passage extending from a first end to a second end, the inner passage sized to receive the shaft of the screw, the first end of the cannula including a tip for engaging the bone, the inside surface including threads engageable with the second threads of the screw when the screw is received by the inner passage of the cannula wherein a bone receiving chamber is defined between the inside surface of the cannula and the outside surface of the screw adjacent the first threads of the screw.

20. A method of bone marrow biopsy, comprising the steps of:

a) providing a screw having first threads and second threads;

b) rotating the first threads into a bone;

c) providing a cannula having an inner passage sized to receive the screw, and threads along a portion of the inner passage;

d) positioning the screw in the inner passage of the cannula;

e) rotating the cannula to threadably engage the threads of the cannula with the second threads of the screw such that a first end of the cannula is inserted into the bone to position a portion of bone in a chamber defined between an inside surface of the cannula and the first threads of the screw;

f) separating the portion of bone from a remainder of the bone; and g) removing the cannula and the screw from the bone.

21. The method of claim 20, further comprising the steps of:

a) providing a stop disposed between the first and second threads on the screw;

b) before the step of inserting the cannula into the bone, rotating the first threads into the bone until an outer surface of the bone is engaged by the stop.

22. A method of treatment of a bone comprising the steps of:

a) providing a screw having an inner passage extending from a head toward a tip, the inner passage exiting the screw at a port, the screw having threads adjacent the tip;

b) rotating the screw into the bone to position the port in an interior of the bone;

c) removing bone marrow from the head of the screw by applying suction to the head such that bone marrow is transported from the bone interior through the port to the inner passage and then to the head;

d) attaching a cannula to the screw and inserting an end of the cannula into the bone to position a portion of the bone between the screw and the cannula; and e) rotating the screw and the cannula together relative to the bone to separate the bone portion from the rest of the bone.

23. A bone screw comprising:

a) a head and a tip; and b) a shaft extending from the head to the tip, the shaft including:
   i) an inner surface defining a passage from the head to the tip, the inner surface including threads located adjacent to the head; and
   ii) an outer surface including first threads located adjacent to the tip, a flute extending from the tip through at least a portion of the first threads, second threads positioned between the head and the first threads, and a stop surface positioned between the first threads and the second threads.

24. The bone screw of claim 23, wherein the inner surface further includes a tool engaging surface portion located adjacent to the head and defining a shape sized to be mated with a rotatable tool having a reciprocal shape, the threads on the inner surface positioned between the tool engaging surface and the second threads.

* * * * *